United States Patent
Moore et al.

(10) Patent No.: US 12,431,039 B2
(45) Date of Patent: Sep. 30, 2025

(54) TESTING SURFACE FOR ADVANCED MEDICAL TRAINING

(71) Applicant: The Penn State Research Foundation, University Park, PA (US)

(72) Inventors: Jason Z. Moore, State College, PA (US); Scarlett Miller, State College, PA (US); Dailen Brown, State College, PA (US); Haroula Tzamaras, State College, PA (US); Jessica M. González-Vargas, State College, PA (US); E. David C. Han, Hummelstown, PA (US)

(73) Assignee: The Penn State Research Foundation, University Park (PA)

( * ) Notice: Subject to any disclaimer, the term of this patent is extended or adjusted under 35 U.S.C. 154(b) by 770 days.

(21) Appl. No.: 17/716,543

(22) Filed: Apr. 8, 2022

(65) Prior Publication Data

US 2022/0327962 A1     Oct. 13, 2022

Related U.S. Application Data

(60) Provisional application No. 63/172,134, filed on Apr. 8, 2021.

(51) Int. Cl.
G09B 23/30     (2006.01)
A61B 34/00     (2016.01)
G09B 23/28     (2006.01)

(52) U.S. Cl.
CPC ............ *G09B 23/285* (2013.01); *A61B 34/25* (2016.02); *G09B 23/30* (2013.01); *A61B 2562/0223* (2013.01)

(58) Field of Classification Search
CPC ...... G09B 23/28; G09B 23/285; G09B 23/30; G09B 23/34
See application file for complete search history.

(56) References Cited

U.S. PATENT DOCUMENTS

| | | | | |
|---|---|---|---|---|
| 5,149,270 A * | 9/1992 | McKeown | ........... | G09B 23/285 434/262 |
| 5,403,191 A * | 4/1995 | Tuason | ................ | G09B 23/285 434/262 |
| 5,425,644 A * | 6/1995 | Szinicz | .................. | G09B 23/28 434/267 |
| 5,873,732 A * | 2/1999 | Hasson | ................ | G09B 23/286 434/262 |
| 5,947,743 A * | 9/1999 | Hasson | ................ | G09B 23/286 434/262 |
| 5,947,744 A * | 9/1999 | Izzat | .................... | G09B 23/285 434/262 |
| 6,850,222 B1 * | 2/2005 | Rosenberg | ............. | G09B 23/28 345/157 |

(Continued)

*Primary Examiner* — Kurt Fernstrom
(74) *Attorney, Agent, or Firm* — Dinsmore & Shohl LLP

(57) ABSTRACT

A medical training system is provided having a housing, a phantom tissue simulant surface, an insertion hole, at least one medical instrument with a tip configured to pierce the phantom tissue simulant surface, a passage, at least one sensor, and a microprocessor. The system simulate a medical training procedure and the microprocessor is configured to read and process information from each of the at least one sensor in order to provide feedback to a user.

18 Claims, 14 Drawing Sheets

(56) References Cited

U.S. PATENT DOCUMENTS

| | | | | |
|---|---|---|---|---|
| 7,997,903 B2* | 8/2011 | Hasson | ............... | G09B 23/285 |
| | | | | 434/262 |
| 8,764,452 B2* | 7/2014 | Pravong | ............... | G09B 23/30 |
| | | | | 434/262 |
| 9,355,574 B2* | 5/2016 | Jian | ..................... | G06T 19/20 |
| 9,418,574 B2* | 8/2016 | Park | ..................... | G09B 23/32 |
| 9,460,638 B2* | 10/2016 | Baker | ............... | G09B 23/285 |
| 9,805,625 B2* | 10/2017 | Feins | ..................... | A61G 13/08 |
| 9,959,785 B2* | 5/2018 | Tortola | ............... | G09B 23/285 |
| 10,943,507 B2* | 3/2021 | Mourton | ............. | G09B 23/285 |
| 11,341,868 B2* | 5/2022 | Horst | ..................... | G09B 23/32 |
| 2007/0166682 A1* | 7/2007 | Yarin | ............... | G09B 23/285 |
| | | | | 434/262 |
| 2010/0167250 A1* | 7/2010 | Ryan | ............... | G09B 23/285 |
| | | | | 434/267 |

* cited by examiner

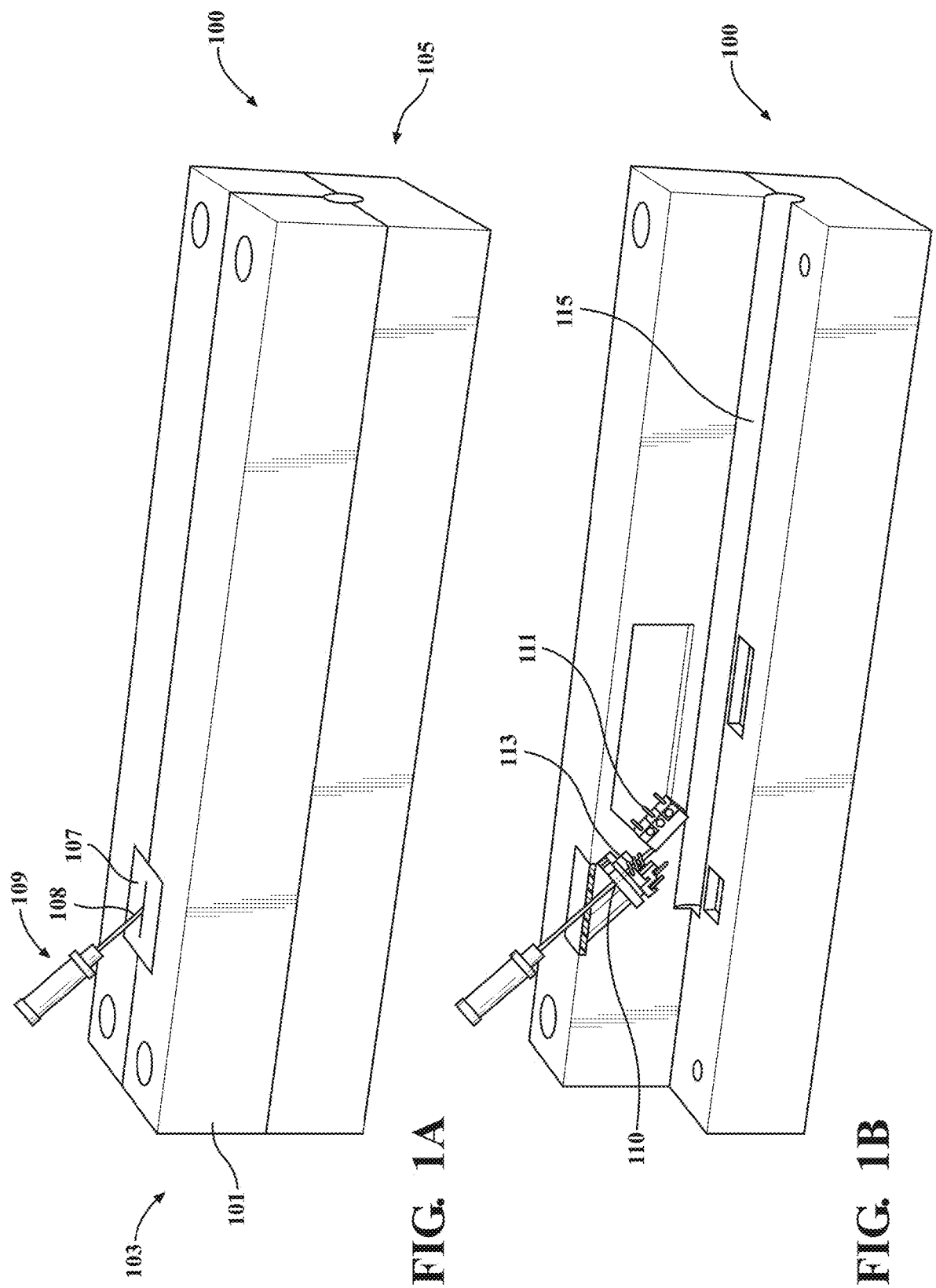

TESTING SURFACE FOR ADVANCED MEDICAL TRAINING

CROSS-REFERENCE TO RELATED APPLICATIONS

This application claims priority to provisional application No. 63/172,134 filed Apr. 8, 2021, the disclosure of which is hereby incorporated by reference in its entirety.

GOVERNMENT SUPPORT

This invention was made with government support under Grant No. HL127316 Awarded by the National Institutes of Health. The Government has certain rights in the invention.

FIELD OF THE INVENTION

The present invention relates to a system and method for medical training and more specifically an advanced testing surface to simulate tissue for a medical procedure and a method of use.

BACKGROUND OF THE INVENTION

Central Venous Catheterization (CVC) is an important procedure that occurs over 5 million times a year in the United States. Hospital training of residents on this procedure traditionally involves observing the procedure, practicing the procedure, and then teaching the procedure. With this model, medical residents are trained by performing procedures on real patients while under supervision. Due to the risk this method involves for patients, many medical centers have expressed a greater interest in simulation methods to allow for repetitive practice and evaluation of procedural steps before the resident performs the procedure in the clinic. Many state of the art simulators have focused training and evaluation on the haptics involved in the procedure, neglecting training on simpler steps and detailed training on the use of the medical instruments involved. Appropriate use of these tools is vital for ensuring sterile technique throughout the procedure which reduces the risk of infection, a complication that is far too common in CVC today.

SUMMARY OF INVENTION

The present invention includes several aspects for the advanced training of medical procedures. Any of the several aspects may be used in any combination with any of the other aspects or with aspects already known for the training of medical procedures. The disclosure and drawings included herein provide further details on aspects of the present invention.

In one aspect, a medical training system includes: a user interface, a housing with a proximal end and a distal end, a phantom tissue simulant surface on a top surface of the housing, an insertion hole at the proximal end and disposed beneath the phantom tissue simulant, at least one medical instrument with a tip, a passage, at least one sensor, and a microprocessor.

In another aspect, a medical training system includes: a user interface, a work surface, a collapsible camera, a phantom tissue simulant surface, a medical comprising medical instruments with a tip, an insertion channel with an opening, at least one sensor, and a microprocessor.

In yet another aspect, a medical training system involves a method including providing a medical training system with a user interface, a work surface, a camera, a phantom tissue simulant surface, a plurality of medical instruments, an insertion channel with an opening, at least one sensor, and at least one microprocessor; locating an insertion hole; performing a medical instrument manipulation by inserting the tip of the needle assembly through the phantom tissue simulant surface and into the insertion hole; sensing that the tip of the needle assembly has penetrated the phantom tissue simulant and the insertion hole and calculating a depth position of the needle assembly within the insertion hole using the at least one sensor; manipulating the needle assembly by disconnecting the syringe and the occlude hub from the needle assembly; providing a guidewire to be inserted into the insertion hole and calculating a depth position of the guidewire within the insertion hole through the at least one sensor; removing the needle from the insertion hole while leaving the guidewire placed in the insertion hole; performing an incision by applying an external downward force to a scalpel into the phantom tissue surface and calculating a depth position of the scalpel within the insertion hole using the at least one sensor; removing the scalpel from the insertion hole and sensing the removal of the scalpel from the insertion hole using the at least one sensor; performing a dilation by placing a dilator through the incision and into the insertion hole and calculating a depth position of the dilator within the insertion hole using the at least one sensor; removing the dilator from the insertion hole and sensing the removal of the dilator from the insertion hole using the at least one sensor; providing a catheter to be inserted into the insertion hole and calculating a depth position of the catheter within the insertion hole using the at least one sensor; removing the guidewire from the insertion hole and sensing the removal of the guidewire using the at least one sensor; securing the catheter in a fixed position within the insertion hole and calculating a depth position of the catheter within the insertion hole using the at least one sensor; and providing performance feedback and assessment using the user interface based on the calculations of the at least one sensor.

BRIEF DESCRIPTION OF THE DRAWINGS

The present disclosure is illustrated by way of example, and is not limited by, the accompanying figures in which like reference numerals indicate similar elements and in which:

FIG. 1A schematically depicts a medical training system with a housing;

FIG. 1B schematically depicts a partial cross-sectional view of the medical training system of FIG. 1A;

DETAILED DESCRIPTION

Figure 2A:
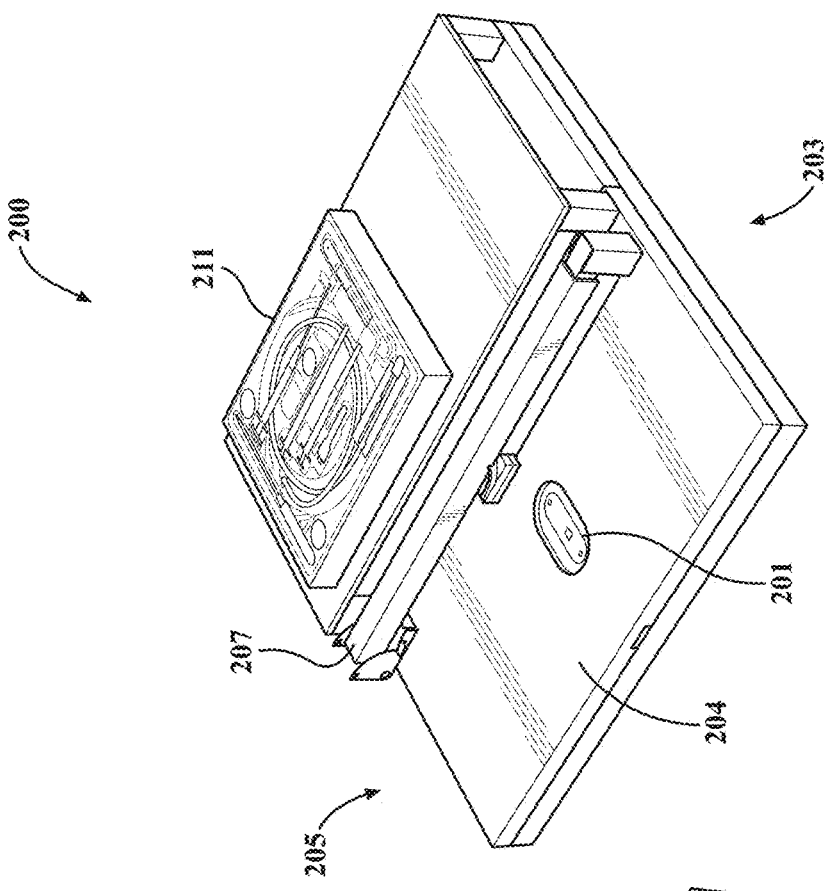
FIG. 2A schematically depicts a medical training system with a work surface and including an expanded camera and medical tray.

According to one aspect of the present invention, a medical training system is provided. This training system may allow a user to practice needle insertion, with one non-limiting example being Central Venous Catheterization (CVC). As more clearly described in the disclosure hereinbelow, the training system may have a user interface, a housing with a proximal end and a distal end, a phantom tissue simulant surface on a top surface of the housing, an insertion hole at the proximal end and disposed beneath the phantom tissue simulant, at least one medical instrument with a tip, a passage, at least one sensor, and a microprocessor. The system may providing sensing for use in training of a user. The phantom tissue simulant surface may be modular and partially or completely replaceable. The tissue surface may be cut by a scalpel and have various medical instruments inserted into it. Disclosed hereinbelow is an advanced surface for a particular procedure, but it is understood that the present invention may be used with any surface for any procedure, with appropriate modifications, as will be clear to those of skill in the art.

As shown in FIGS. 1A and 1B, the medical training system 100 includes a housing 101 extending in a longitudinal direction. FIG. 1A illustrates the training system 100 as assembled while FIG. 1B has a portion removed to show internal structure. The housing 101 has a proximal end 103 and a distal end 105. A phantom tissue simulant surface 107 is disposed on a top surface of the housing 101. The housing has an insertion hole 110 disposed beneath the phantom tissue simulant 107. FIGS. 1A and 1B show a medical instrument 109. The medical instrument 109 will have a have a tip configured to pierce the phantom tissue simulant surface 107. Passage 115 extends from the insertion hole 110 in the longitudinal direction of the housing 101. At least one sensor is operable to determine an insertion position of the tip of medical instrument 109 and to sense an external downward force of the medical instrument 109 onto the phantom tissue simulant surface 107. In embodiments the sensors include spring loaded push pins 113 and limit switch 111.

Phantom tissue simulant surface 107 can consists of any suitable material. In embodiments phantom tissue simulant surface 107 is a silicone phantom tissue simulant surface.

Medical instrument 109 can include a needle assembly, a guidewire, a scalpel, a dilator, and a catheter. For example, medical instrument 109 can be an 18-gauge needle. Medical instrument 109 has a tip 108 for penetrating phantom tissue simulant surface 107. The tip 108 of the needle assembly and the scalpel can be blunted for training purposes in order to promote safety and prevent any damage.

Spring loaded push buttons 113 and a limit switch 111 can be placed within the insertion hole 110, and configured to detect insertion and removal of tip 108 of medical instrument 109.

Figure 2B:
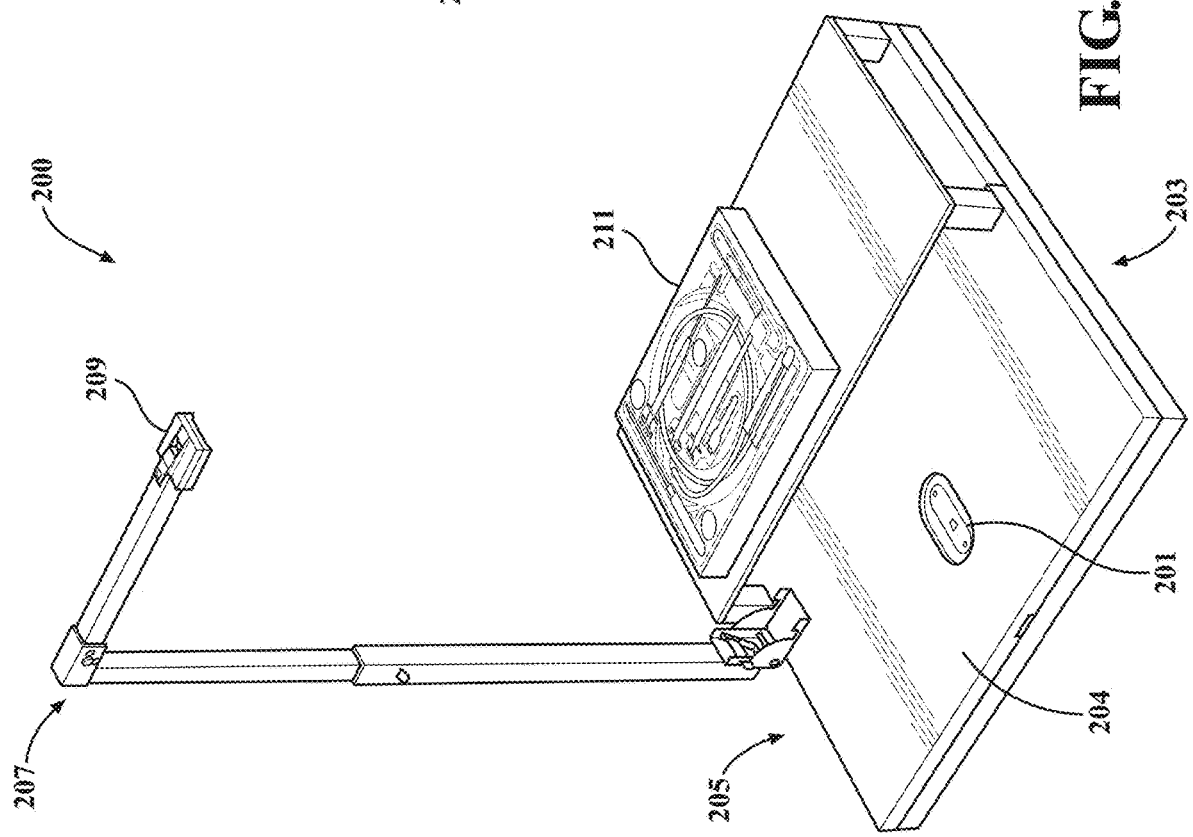
FIG. 2B schematically depicts a medical training system with a work surface and including a collapsed camera and medical tray.

FIGS. 2A and 2B show a medical training system 200. In this embodiment phantom tissue simulant 201 is positioned on a top of a work surface 204. Work surface 204 may have a proximal end 203 and a distal end 205. Work surface 204 may also have a medical tray 211 including various medical instruments. Work surface 204 may also include a camera assembly 207 with a lens 209 capable of viewing work surface 204. The camera assembly 207 is shown in an expanded position in FIG. 2A and in a collapsed position in FIG. 2B. In the expanded position, the lens can view the work surface and the medical tray 211. Medical tray 211 can hold various medical instruments for performing a training procedure. The background color of medical tray 211 can enable a computer vision algorithm to distinguish between various medical instruments on medical tray 211. Each of the various medical instruments may include a tip configured to pierce the phantom tissue simulant 201.

Figure 3A:
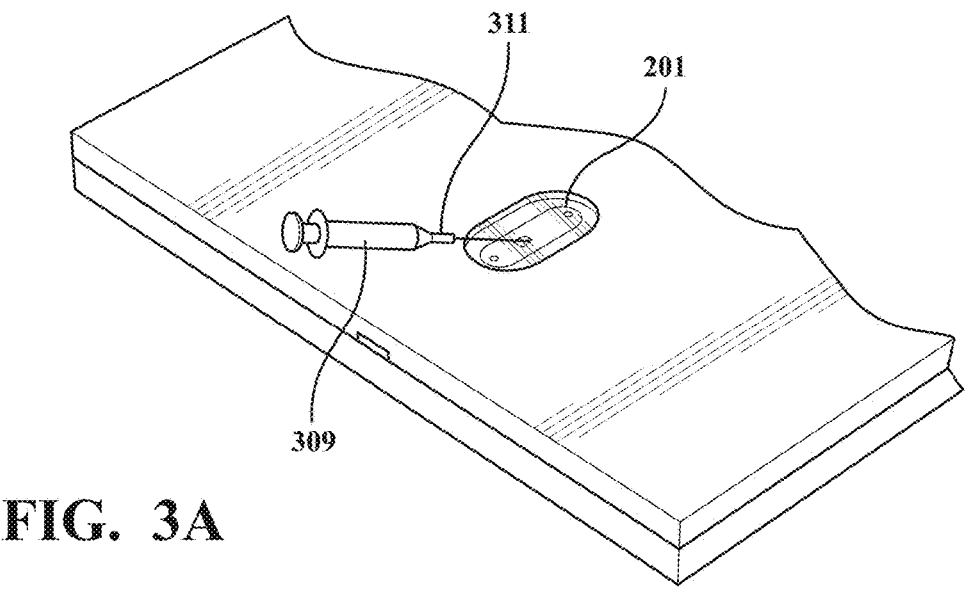
FIGS. 3A-C schematically depict various views of a needle assembly in a medical training system.
Figure 3B:
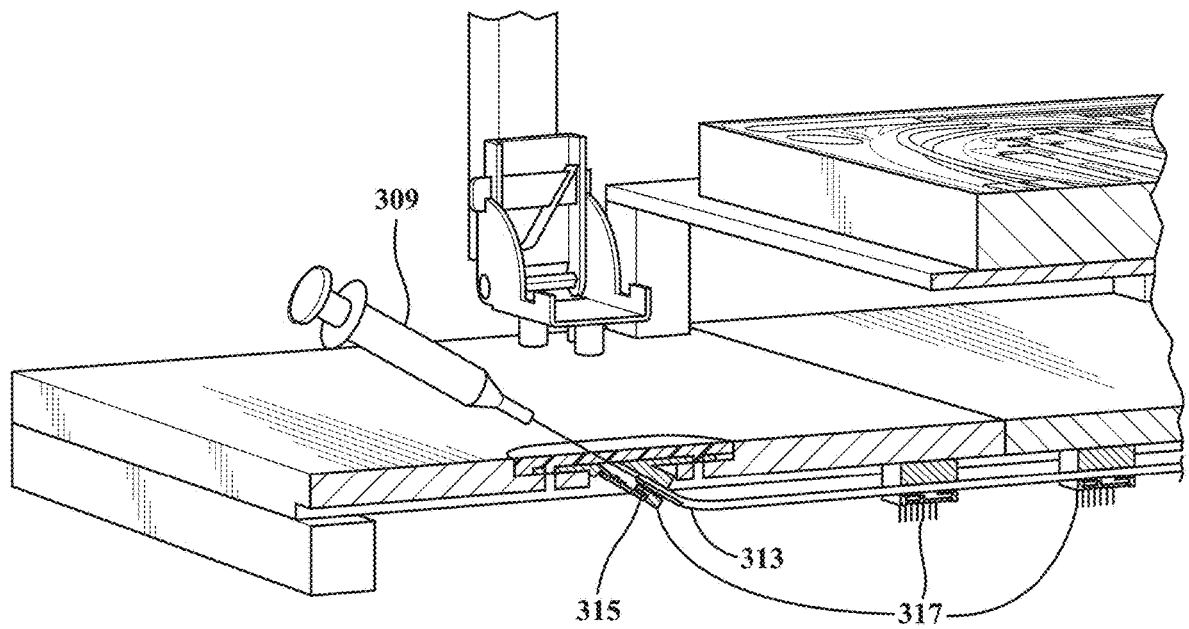
Figure 3C:
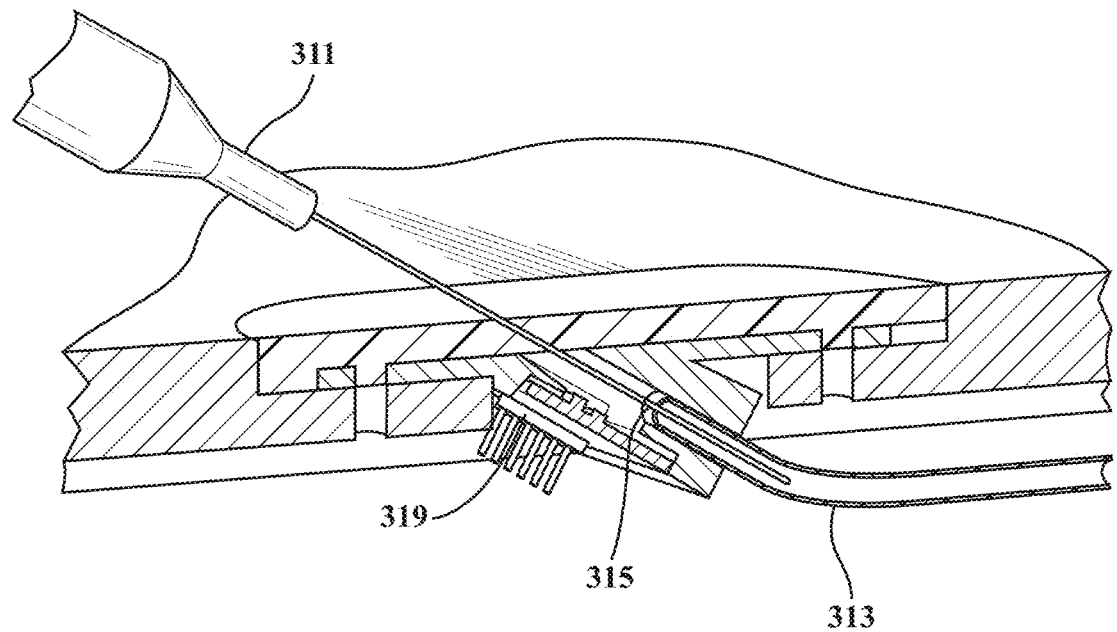

FIGS. 3A-C show the use of a needle assembly 309 with the medical training system 200. The needle assembly 309 includes a tip configured to pierce the phantom tissue simulant 201. In embodiments, the tip of needle assembly 309 is blunted.

An opening 315 of an insertion channel 313 is disposed beneath the phantom tissue stimulant simulant 201. The insertion channel 313 extends from the opening 315 to an opposite distal end. The insertion channel 313 has a plurality of sensors 317 operable to determine an insertion position of the tip of the various medical instruments and to sense an external downward force of the various medical instrument on the phantom tissue simulant surface 201. Therefore in FIGS. 3A-C, the plurality of sensors 317 are operable to sense an external downward force of the needle assembly 309 on the phantom tissue simulant surface 201 and to determine an insertion position of the tip of needle assembly 309 within the insertion channel 313. One of the sensors 317 can be an entry sensor 319.

Figure 4A:
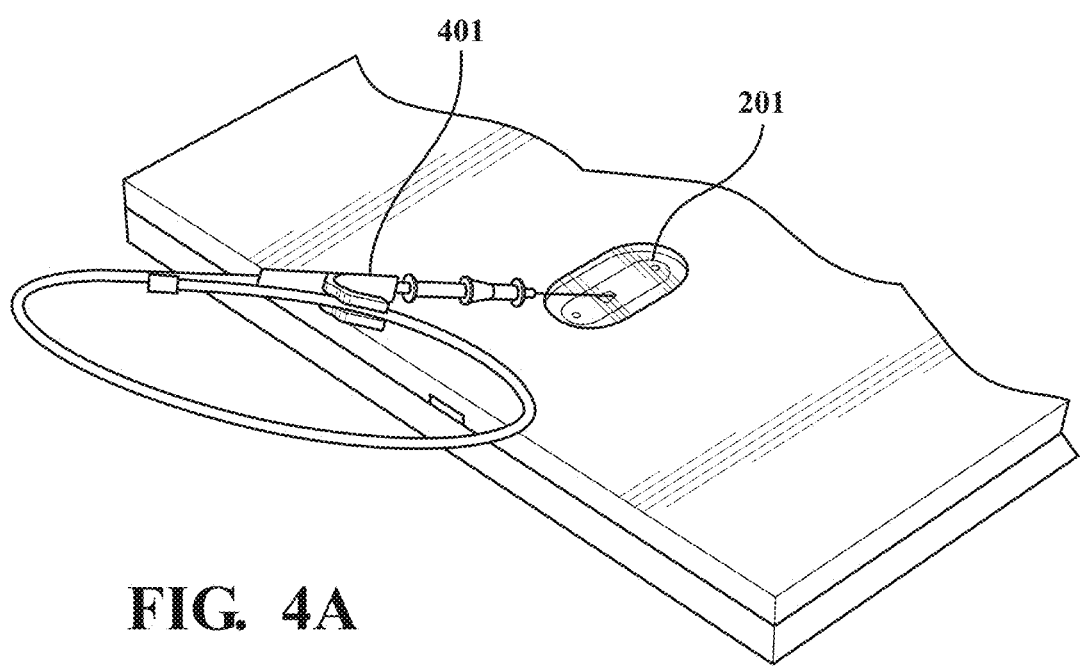
FIGS. 4A-B schematically depict various views of a guidewire in a medical training system.
Figure 4B:
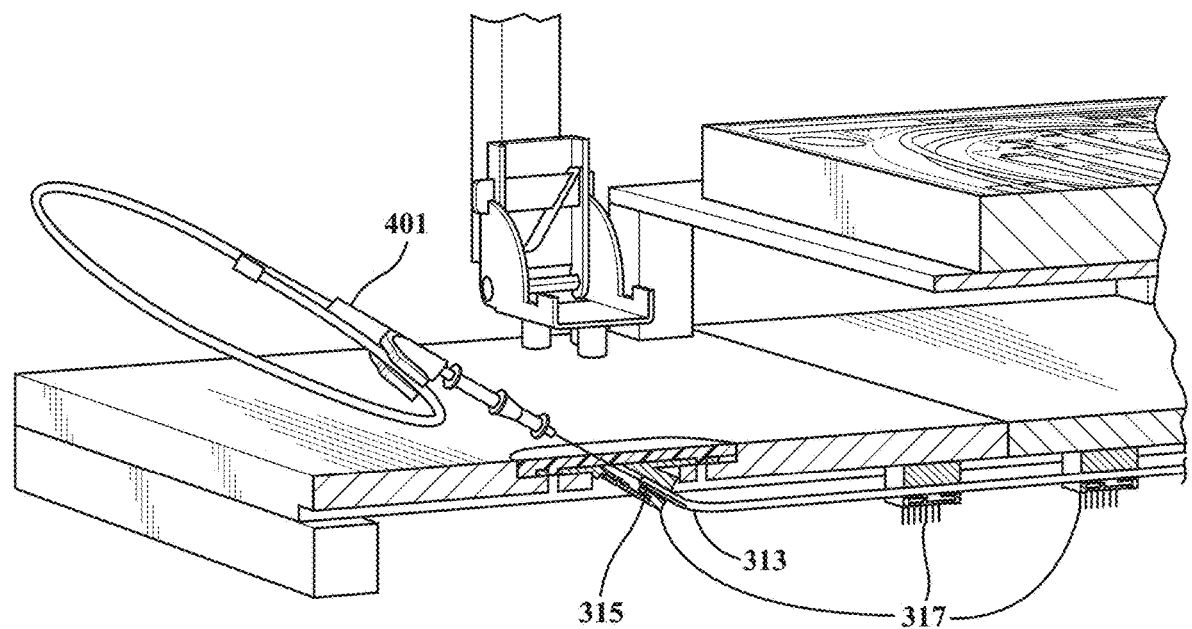

FIGS. 4A-B show the use of a guidewire 401 in the medical training system 200. The guidewire 401 includes a tip configured to pierce the phantom tissue simulant 201. Opening 315 of an insertion channel 313 is still disposed beneath the phantom tissue stimulant simulant 201. The insertion channel 313 extends from the opening 315 to an opposite distal end 325. In FIGS. 4A-B, the plurality of sensors 317 are operable to sense an external downward force of guidewire 401 on the phantom tissue simulant surface 201 and to determine an insertion position of the guidewire 401 within the insertion channel 313.

Figure 5A:
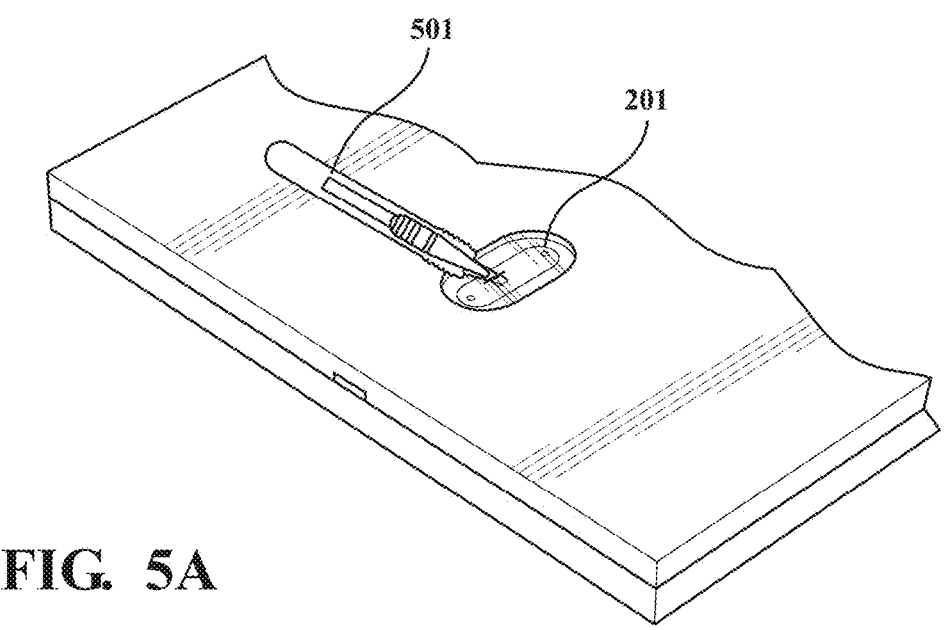
FIGS. 5A-C schematically depict various views of a scalpel in a medical training system.
Figure 5B:
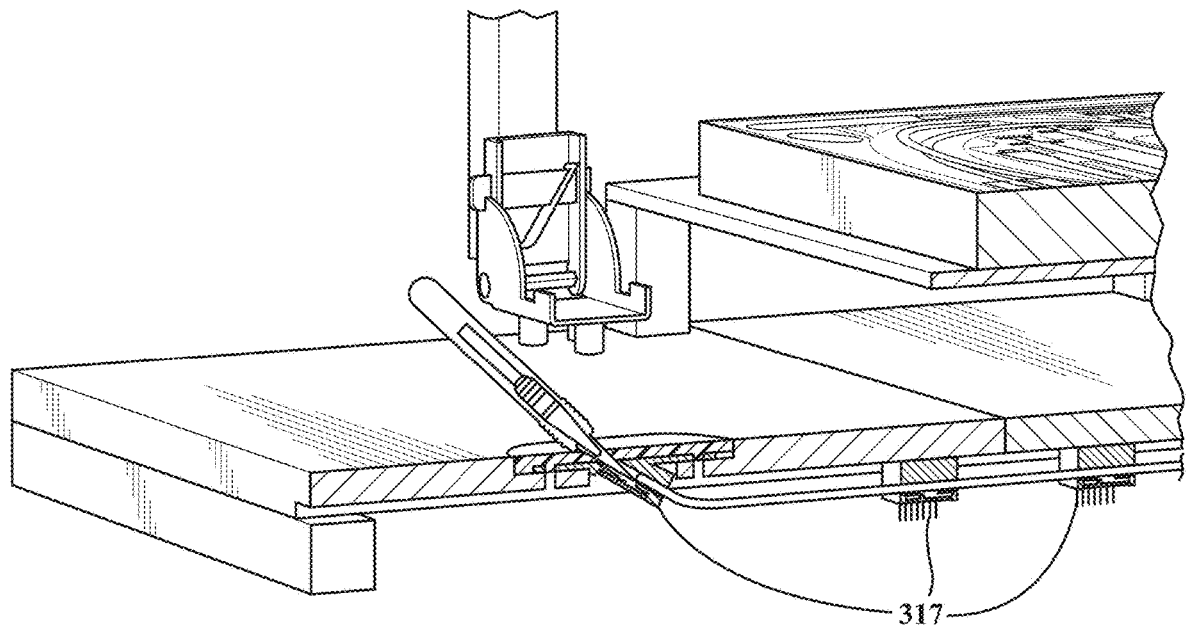
Figure 5C:
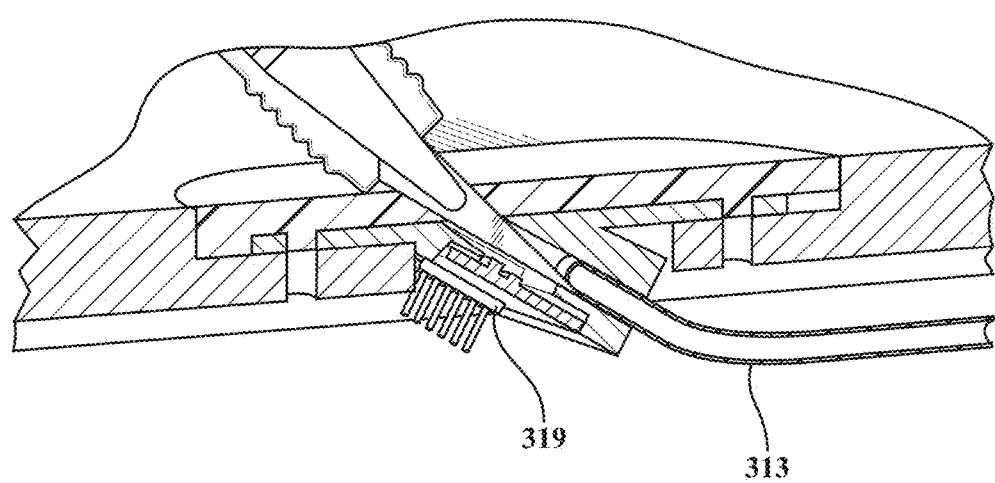

FIGS. 5A-C show the use of a scalpel 501 in the medical training system 200. The scalpel 401 includes a tip configured to pierce the phantom tissue simulant 201. Opening 315 of an insertion channel 313 is still disposed beneath the phantom tissue stimulant simulant 201. The insertion channel 313 extends from the opening 315 to an opposite distal end 325. In FIGS. 5A-C, the plurality of sensors 317 are operable to sense an external downward force of scalpel 501 on the phantom tissue simulant surface 201 and to determine an insertion position of the scalpel 501 within the insertion channel 313.

Figure 6A:
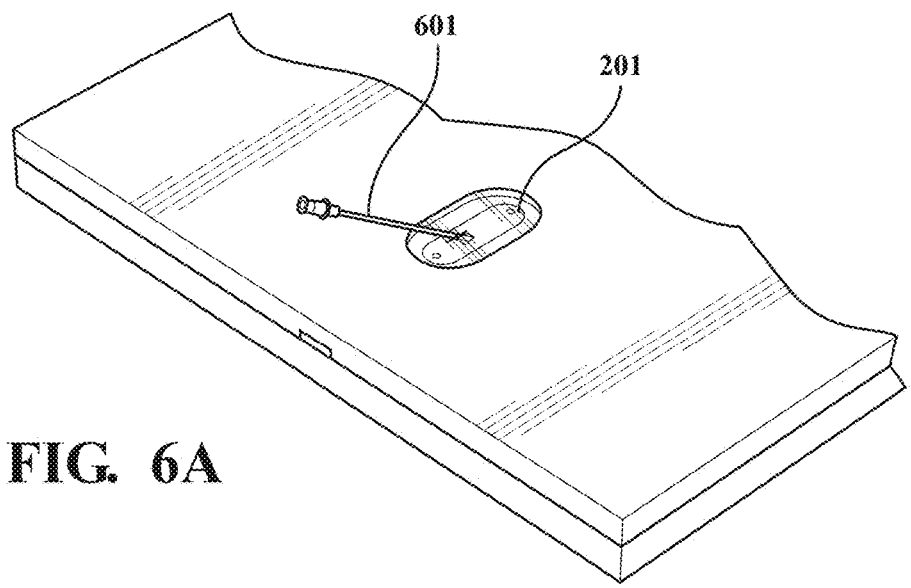
FIGS. 6A-C schematically depict various views of a dilator in a medical training system.
Figure 6B:
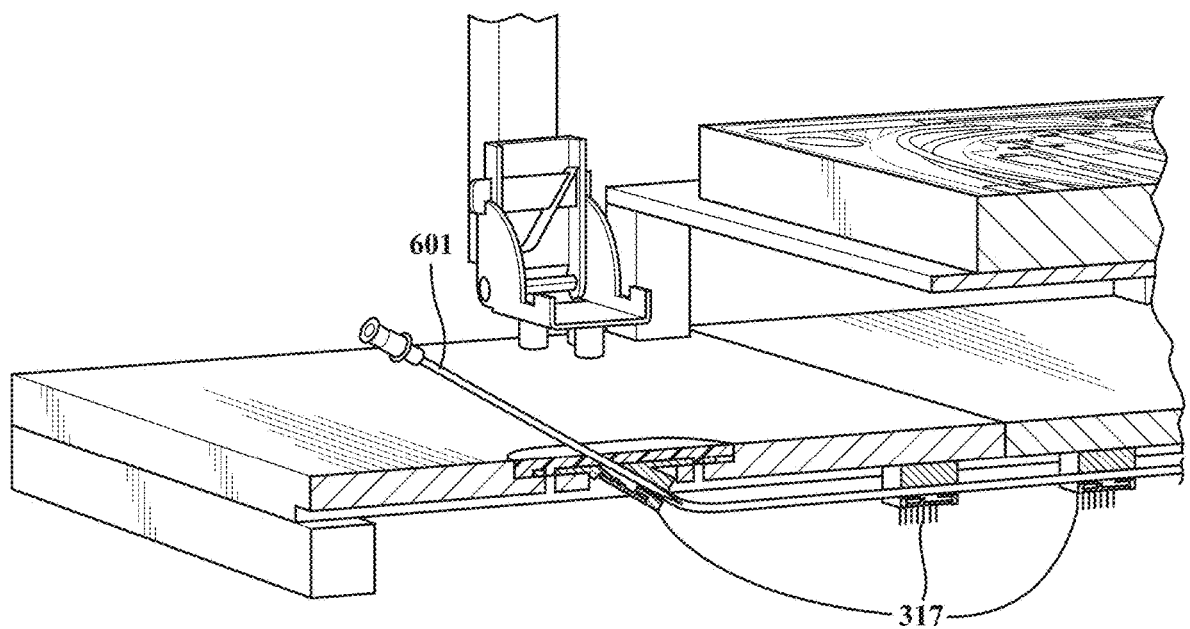
Figure 6C:
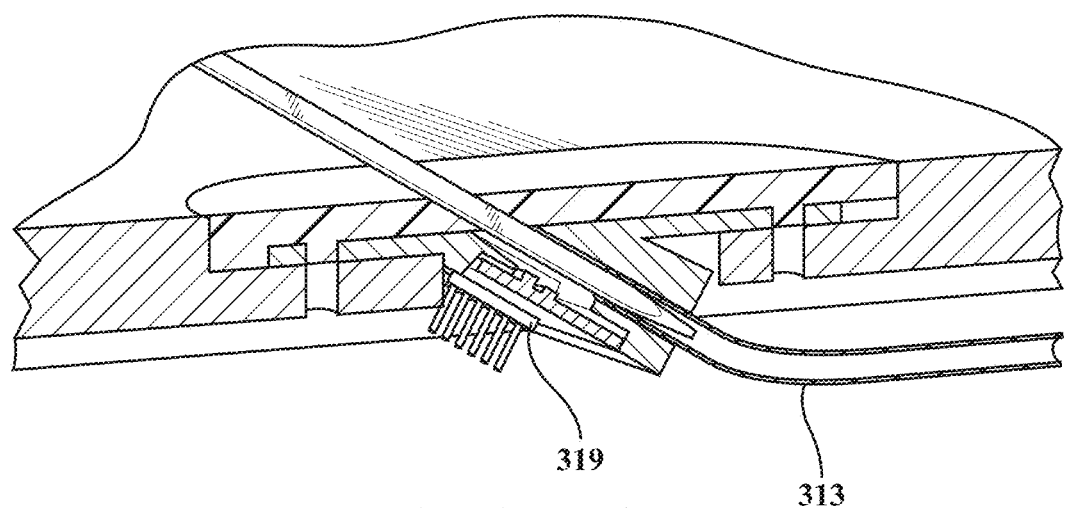

FIGS. 6A-C show the use of a dilator 601 in the medical training system 200. The dilator 601 includes a tip configured to pierce the phantom tissue simulant 201. Opening 315 of an insertion channel 313 is still disposed beneath the phantom tissue stimulant simulant 201. The insertion channel 313 extends from the opening 315 to an opposite distal end 325. In FIGS. 6A-C, the plurality of sensors 317 are operable to sense an external downward force of dilator 601 on the phantom tissue simulant surface 201 and to determine an insertion position of the dilator 601 within the insertion channel 313.

Figure 7A:
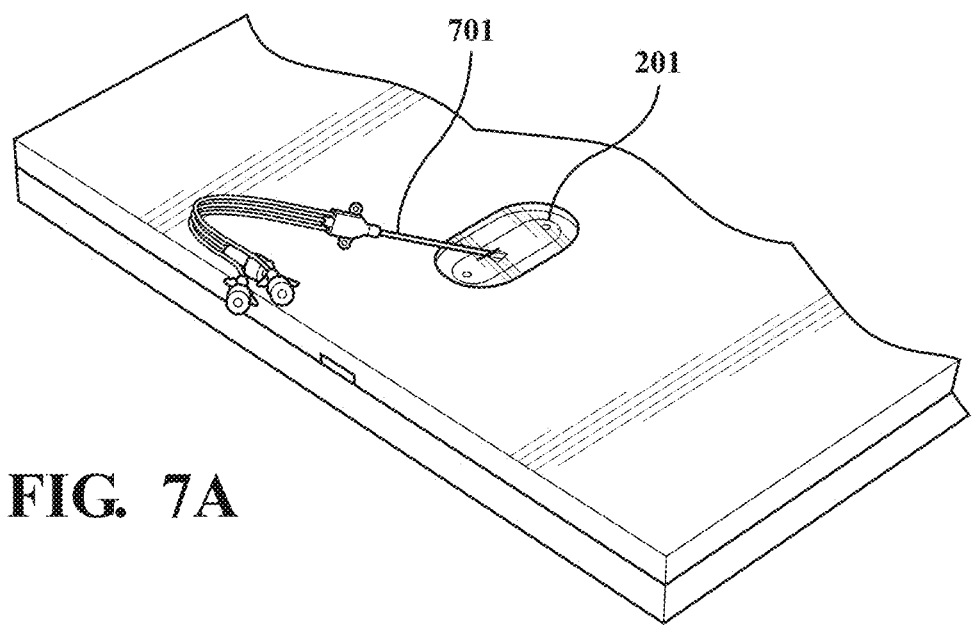
FIGS. 7A-C schematically depict various views of a catheter in a medical training system.
Figure 7B:
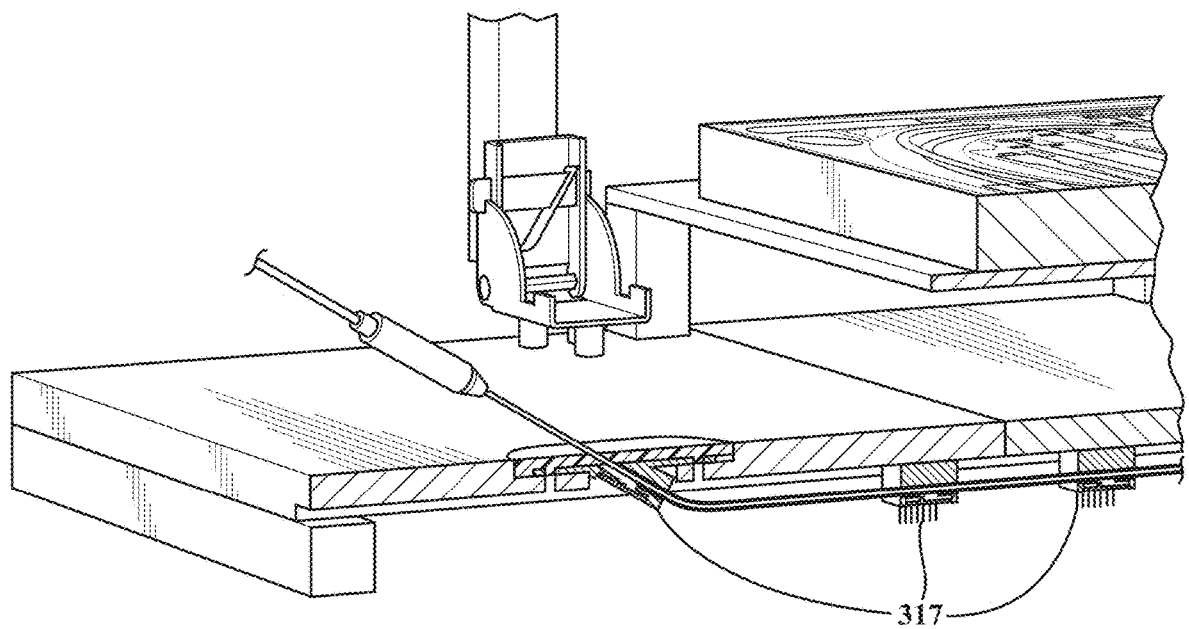
Figure 7C:
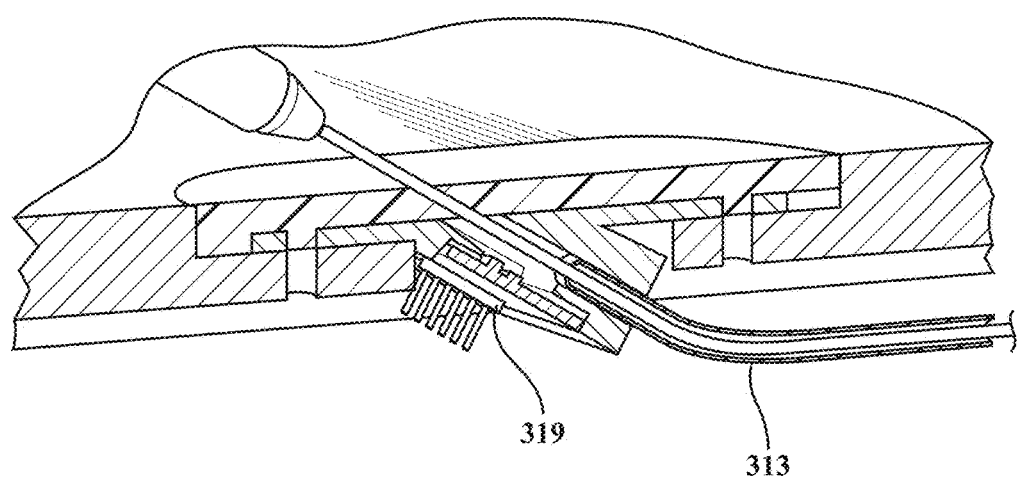

FIGS. 7A-C show the use of a catheter 701 in the medical training system 200. The catheter 701 includes a tip configured to pierce the phantom tissue simulant 201. Opening 315 of an insertion channel 313 is still disposed beneath the phantom tissue stimulant simulant 201. The insertion channel 313 extends from the opening 315 to an opposite distal end 325. In FIGS. 7A-C, the plurality of sensors 317 are operable to sense an external downward force of catheter 701 on the phantom tissue simulant surface 201 and to determine an insertion position of the catheter 701 within the insertion channel 313.

Figure 8:
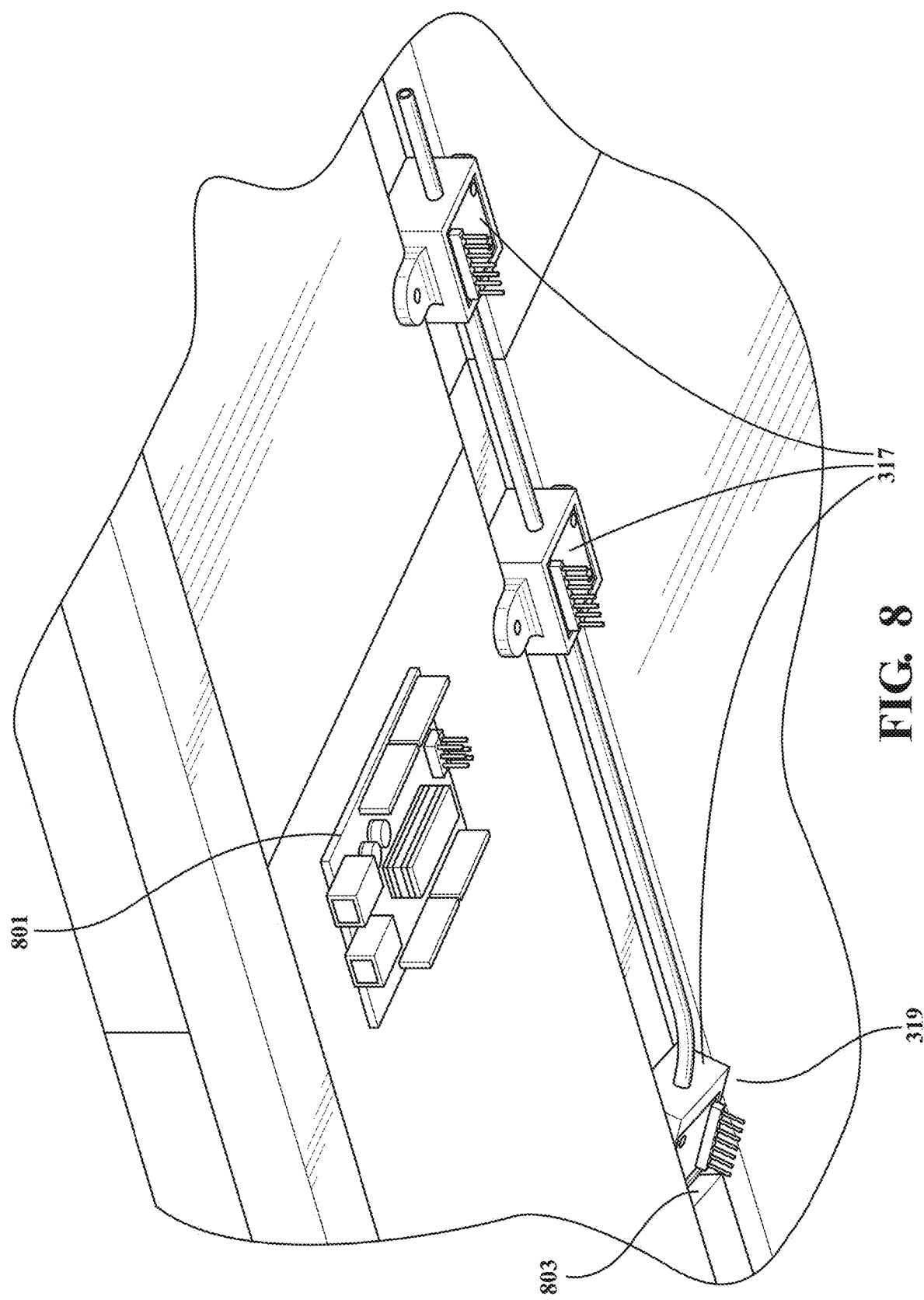
FIG. 8 schematically depicts a processor and sensor array for use with certain embodiments of the present invention.
Figure 9B:
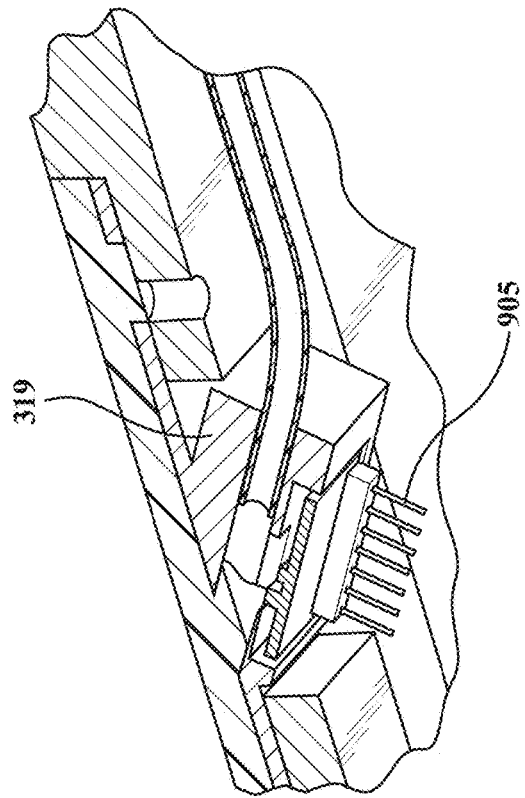
FIG. 9A-D schematically depict various views of sensors for use with certain embodiments of the present invention.
Figure 9D:
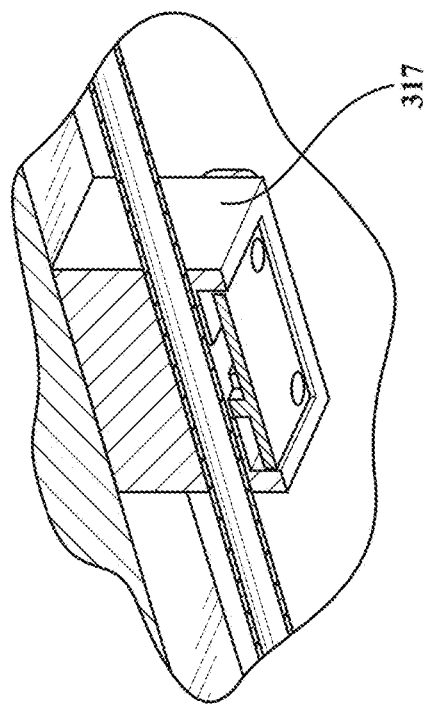
Figure 9A:
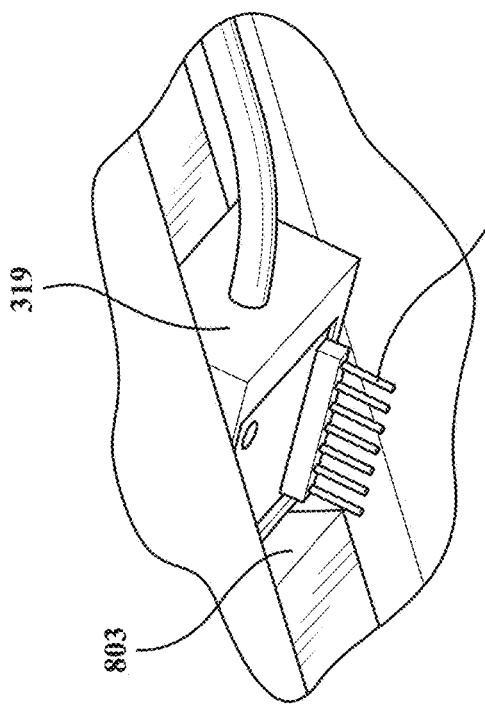
Figure 9C:
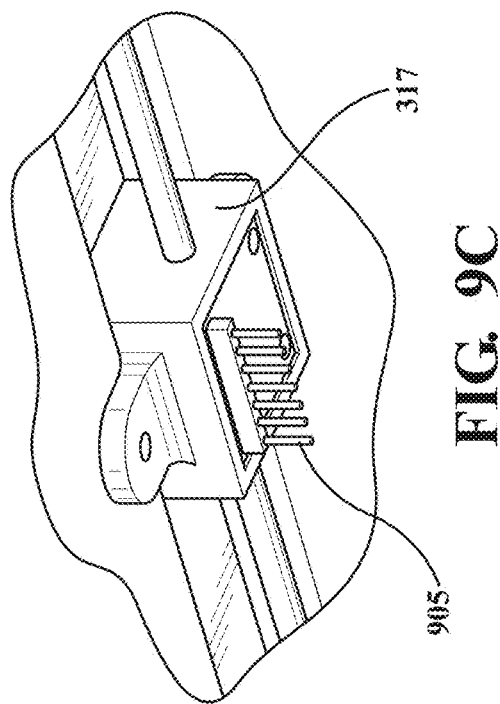

FIG. 8 is an underneath view of the work surface 204. The plurality of sensors 317 are shown. Entry sensor 318 is also shown to be within a cavity 803 of the work surface 204. A microprocessor 801 is used to read and process information from the sensors 317. FIGS. 9A-D show various views of the plurality of sensors 317. FIG. 9A shows a close up view of entry sensor 319 with output signal wires 905. FIG. 9B shows entry sensor 319 in a cross sectional view with output signal wires 905. FIG. 9C shows a close up view of sensor 317 with output signal wires 905. FIG. 9D shows sensor 317 in a cross sectional view without output signal wires 905.

Sensors can sense catheter 701 and accurately detect position of the catheter 701 along the channel 313. Sensors can be of several different types. For example, sensors can be optical sensors, such as RGB color sensors to sense the position of various medical instruments based on a visual color of medical instrument. In embodiments, photosensors could be used similarly to RGB sensors. Photosensors sense the amount of light that would change as an object is passed over it, such as guidewire 401 or catheter 701. Further embodiments of sensors for sensing position and introduction of various medical instruments include a mechanical button that gets pressed as various medical instruments are introduced; an overhead video camera that tracks the movement of the various medical instruments and their positioning; hall effect sensors with magnetized tools that sense the position of various medical instruments inside the passage 115, channel 313, work surface 204, or medical tray 211; and RFID sensors to sense tool position when various medical instruments have RFID tags. RFID sensors provide outputs related to the visual color of an object. For example they allow the use of color to distinguish if the user is inserting the guidewire 401 or the catheter 701. Passage 115 or channel 313 can have a series of these sensors at different locations. The detection of the guidewire 401 or catheter 701 can be sensed by the sensors as they pass by.

Figure 10:
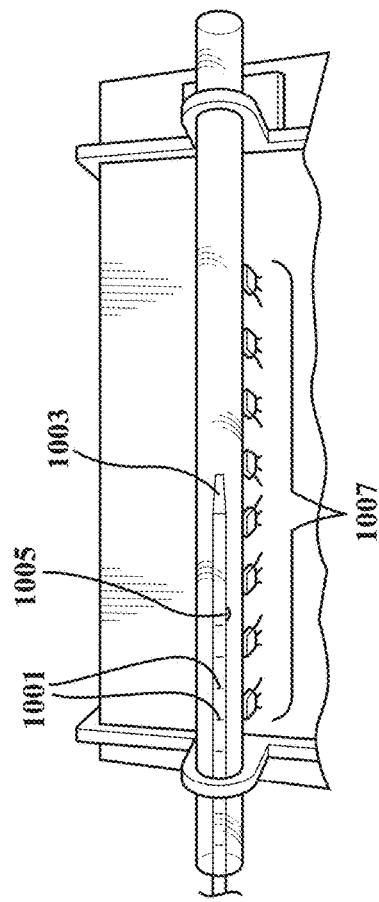
FIG. 10 schematically depicts a catheter inserted into a training system in accordance with the present invention.

Sensors 317 can also be hall effect sensors, such as 49E hall effect sensors, configured to convert information into electrical signals by measuring a changing voltage when the sensors 317 are placed in a magnetic field. Sensors 317 can detect the magnetic field and sense the position of various medical instruments. FIG. 10 shows a hall effect array 1007 that can be used and evaluated using tubing 1111, such as a 12 cm piece of 7.5 mm diameter transparent plastic tubing, mounted over a breadboard with 8 hall effect sensors in an array as shown in FIG. 10. FIG. 10 shows a catheter 701 with a tip 1003 within such a tubing 1111. Magnet 1005, such as a 2.5 mm diameter spherical magnet is positioned on catheter 701. Markings 1001 can be drawn on the catheter 701, such as at every 5 mm, starting from the location of the magnet 1005. Arduino nano 1009 is used to read and process information from each of the hall effect sensors 1007.

Measurement can be done either statically or dynamically. In a static test, the catheter can be inserted and held in place while number of measurements are take. For example, 30 measurements can be taken at 10 Hz. This can be done at 5 mm increments from a position of 0 to 85 mm. In a dynamic test, the catheter can be continuously inserted the full 85 mm at a rate of 5 mm/s while measurements are recorded at 10 Hz. Each test was repeated 5 times.

Figure 12:
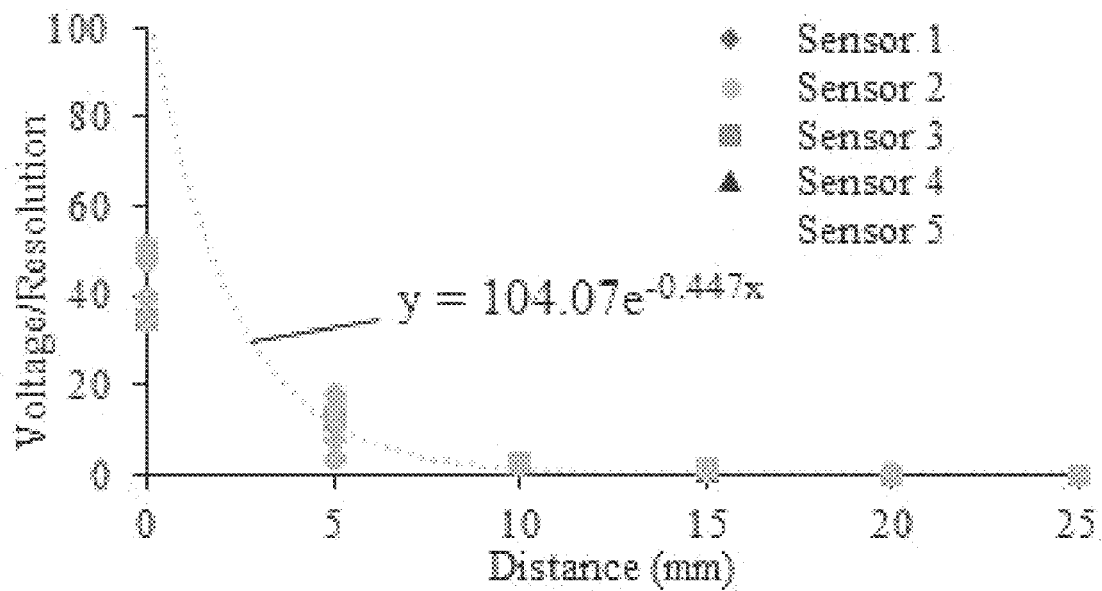
FIG. 12 depicts a plot of voltage resolutions for various sensors with respect to a distance from a magnet in accordance with one or more example embodiments.

In embodiments, hall effect sensors can be placed with their centers 1 cm apart being 1 cm from an opening. The distance from the magnet 1005 to each sensor is calculated from the measured voltage using the following equation (1):

$$d = \frac{\ln\left(\frac{V}{AR}\right)}{B}, \quad (1)$$

where d is the distance, V is the voltage, R is the resolution of the microcontroller, and A and B are experimentally determined constants. A and B are calculated by recording the voltage read by the Arduino Nano in five trials for individual hall effect sensors with the magnet 1005 at varying distances from the center of the sensor. A plot of these results can be seen in FIG. 12. Constants A and B for these sensors, with and R2 value of 0.86, are 104.07 and −0.447 respectively. The maximum distance these sensors can read with a magnet of this size is found to be 15 mm.

The difference in values from the dashed line and the experimental values at distances close to zero are mitigated by using measurements from multiple sensors as defined in equation (2) below. The insertion distance along the insertion channel is calculated by comparing the distances read by consecutive pairs of hall effect sensors in the array. This is accomplished through the following conditional equation:

$$D = \begin{cases} P_1 - d_1 & \text{only } d_1 > 0 \\ \frac{(P_n - d_n) + (P_{n-1} - d_{n-1})}{2} & d_n, d_{n-1} > 0, \\ P_8 + d_8 & \text{only } d_8 > 0 \end{cases} \quad (2)$$

where D is the insertion distance, Pn is the position of the nth sensor in the array, and dn is the distance read by the nth sensor as defined in equation (1).

Figure 13:
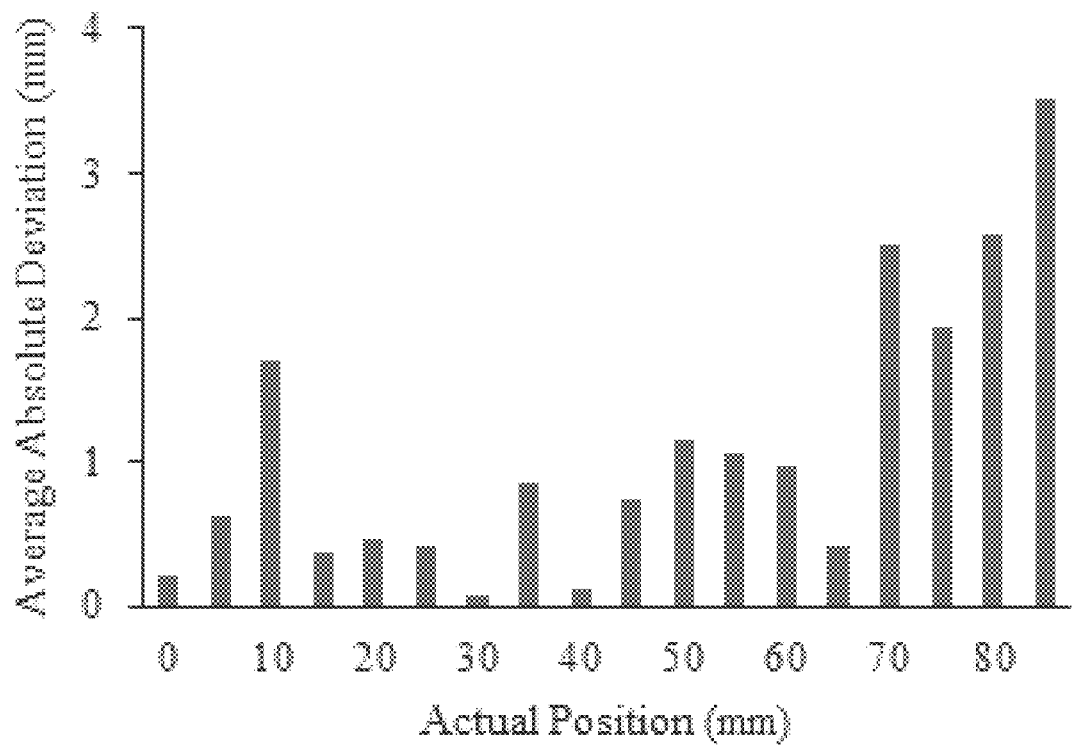
FIG. 13 depicts a graphical illustration of average results of static measurements in accordance with one or more example embodiments.

The average results of static measurements are shown in FIG. 13. The maximum deviation between the distance measured by the hall effect array and the actual position of the catheter is 3.5 mm, with an average absolute deviation of 1.1 mm. It can be seen from the graph in FIG. 13 that the highest inaccuracies occur at the distal end of a sensor array. This is expected because the calculations at this position rely on the measurements of only one sensor to calculate distance. Positions under 10 mm are also calculated based upon measurements from a single sensor; however, errors in this position are mitigated by the constraints of equation (2) which result in distance calculations of zero when the magnet 1005 is out of range. Thus, calculation error at the start of the array is significantly lower than at the end. Errors from single sensor-based calculation at the start of the array appear instead at the 10 mm position, which always underestimated the actual position with an average deviation of 1.7 mm.

Figure 14:
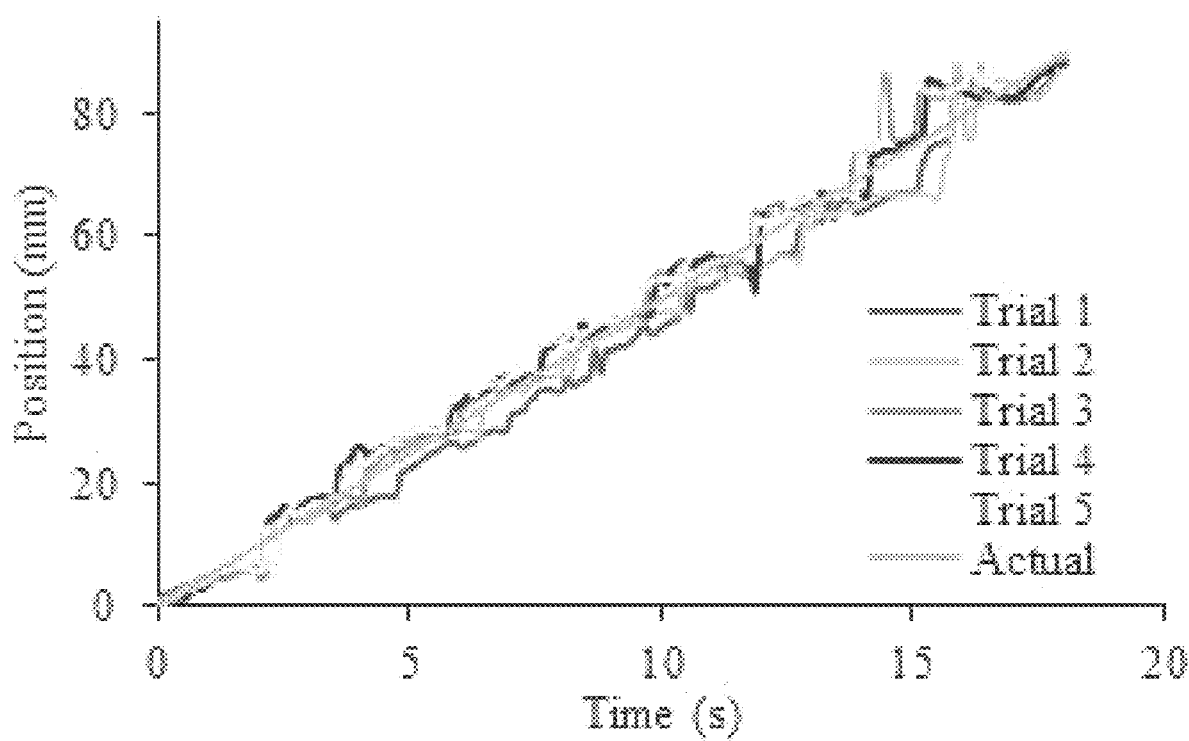
FIG. 14 depicts a graphical illustration of a dynamic measurement in accordance with one or more example embodiments.

Dynamic measurement, as shown in the graph in FIG. 14, provide similar results. In each trial, the greatest inaccuracies are found near the end of the array 1007 where only one hall effect sensor is detecting the magnet 1005. Similarly, trials underestimate the position of the catheter 701 as it approached 10 mm. It can be seen however, that the overall trend of each insertion closely follows the actual position of the catheter 701 as it advanced through the tubing 1111.

An exemplary average speed of each insertion can be found in the table below. The largest deviation in measured insertion speed at 5 mm/s was an overestimate of 0.36 mm/s, with an overall average measured speed of 5.07 mm/s. Further accuracy could be obtained through the use of more hall effect sensors to ensure that all desired positions are calculated using more than one sensor measurement. Furthermore, longer measuring lengths are possible through the use of longer sensor arrays as the accuracy of measurement was consistent along the central portion of the channel.

| Insertion | Average Measured Speed |
| --- | --- |
| Insertion 1 | 4.99 |
| Insertion 2 | 4.92 |
| Insertion 3 | 5.36 |
| Insertion 4 | 4.87 |
| Insertion 5 | 5.22 |

Therefore hall effect sensors 1007 in an array to detect the insertion position of a catheter 701 is appropriately accurate for CVC training purposes. On average, the static position measurements are accurate to ±1.1 mm and the velocity measurements are accurate to 0.16 mm/s. The tip 1003 of the catheter 701 can be placed in the lower third of the superior vena cava (SVC), which is the ideal position for the tip 1003 of a catheter 701.

Figure 11:
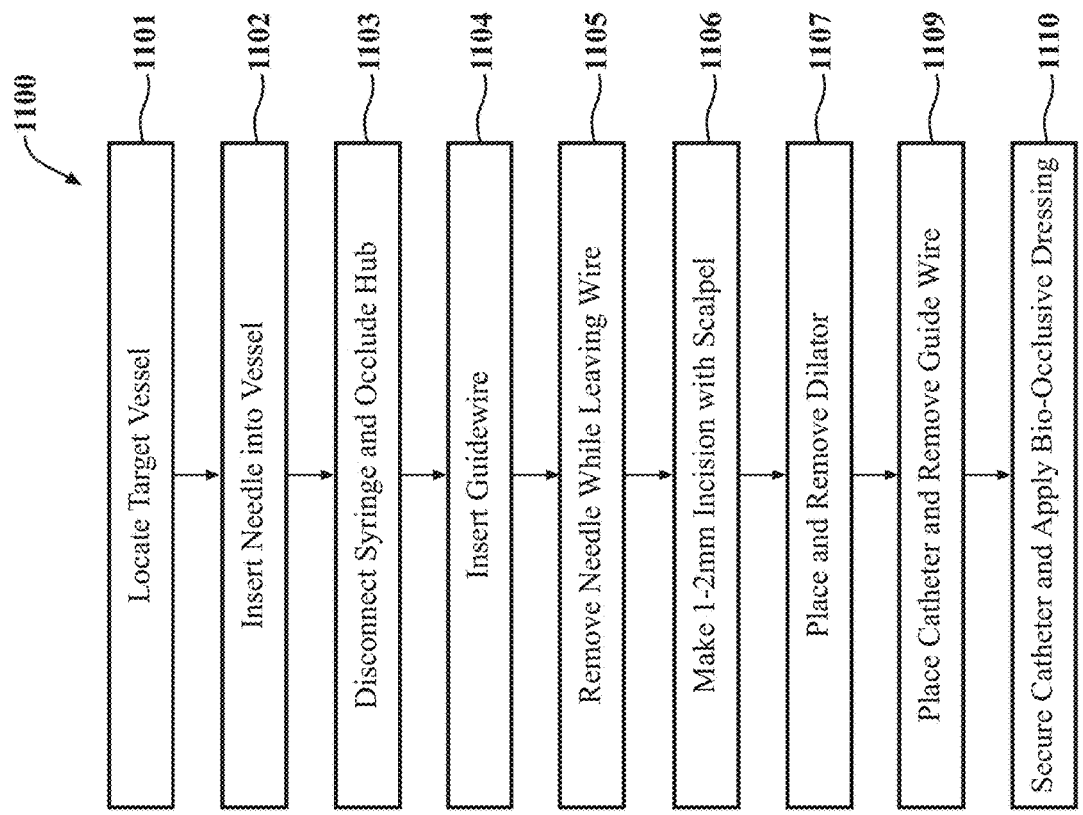
FIG. 11 depicts a flow diagram of example method steps performing a medical training procedure in accordance with one or more example embodiments.

FIG. 11 shows a flow diagram of example method 1100 steps for performing a medical training procedure. At step 1101, an insertion hole is located beneath a phantom tissue simulant surface that simulates a target vessel. At step 1102, the tip of the needle assembly is inserted through the phantom tissue simulant surface and into the insertion hole. The system will sense that the tip of the needle assembly has penetrated the phantom tissue simulant and the insertion hole and calculate a depth position of the needle assembly within the insertion hole using the sensors. At step 1103, a syringe and an occlude hub is disconnected from the needle assembly. At step 1104, a guidewire is inserted into the insertion hole and a depth position of the guidewire within the insertion hole is calculated through the at least one sensor. At step 1105, the needle is removed from the insertion hole while the guidewire is left in place in the insertion hole. At step 1106, an external downward force is applied to a scalpel to perform an incision into the phantom tissue surface. Sensors will calculate a depth position of the scalpel within the insertion hole. At step 1107, the scalpel is removed from the insertion hole. Sensors will sense the removal of the scalpel from the insertion hole. At step 1108, a dilation is performed by placing a dilator through the incision and into the insertion hole. Sensors will calculate a depth position of the dilator within the insertion hole an d the dilator is removed from the insertion hole and sensors will sensing the removal of the dilator from the insertion hole. At step 1009, a catheter is inserted into the insertion hole. Sensors calculate a depth position of the catheter within the insertion hole.

A user interface can provide performance feedback and assessment on the procedure based on the calculations of the at least one sensor.

What is claimed is:

1. A medical training system, comprising:
   a user interface;
   a housing extending in a longitudinal direction, the housing having a proximal end and a distal end;
   a phantom tissue simulant surface on a top surface of the housing;
   the housing having an insertion hole at the proximal end, the insertion hole disposed beneath the phantom tissue simulant;
   at least one medical instrument, the medical instrument having a tip configured to pierce the phantom tissue simulant surface;
   a passage extending from the insertion hole, the passage extending in the longitudinal direction of the housing;
   at least one sensor operable to determine an insertion position of the tip of the at least one medical instrument and to sense an external downward force of the at least one medical instrument on the phantom tissue simulant surface; and
   a microprocessor connected to the at least one sensor, the microprocessor configured to read and process information from each of the at least one sensor.

2. The system of claim 1, wherein the phantom tissue simulant surface consists of a silicone phantom tissue simulant surface.

3. The system of claim 1, wherein the at least one medical instrument, includes a needle assembly, a guidewire, a scalpel, a dilator, and a catheter, the needle assembly and the scalpel being blunted.

4. The system of claim 3, further comprising a magnet connected to the catheter to allow for magnetic position detection using the at least one sensor.

5. The system of claim 1, wherein the at least one sensor includes an entry sensor and one or more additional sensors disposed along the passage.

6. The system of claim 1, wherein the at least one sensor includes a plurality of spring loaded push buttons and a limit switch, both the plurality of spring loaded push buttons and the limit switch placed within the insertion hole, and configured to detect insertion and removal of the at least one medical instrument.

7. The system of claim 1, wherein the at least one sensor comprises hall effect sensors.

8. A medical training system, comprising:
   a user interface;
   a work surface;
   a camera configured to view the work surface;
   a phantom tissue simulant surface disposed in or on the work surface and in view of the camera;
   a medical tray in view of the camera, the medical tray comprising at least one medical instrument, wherein each of the at least one medical instruments includes a tip, the tip of at least one of the medical instruments configured to pierce the phantom tissue simulant;
   an insertion channel disposed beneath the phantom tissue stimulant surface, the insertion channel having an opening of the insertion channel, the insertion channel extending from the opening to a distal end;
   at least one sensor operable to determine an insertion position of the tip of the at least one of the medical instruments and to sense an external downward force of the at least one medical instrument on the phantom tissue simulant surface; and a microprocessor in connection with the at least one sensor, the microprocessor configured to read and process information from each of the at least one sensors.

9. The system of claim 8, wherein the camera includes a collapsed position and an expanded position wherein a lens of the camera is positioned to view the work surface while in the expanded position.

10. The system of claim 8, further comprising a housing for the insertion channel, the at least one sensor, and the microprocessor.

11. The system of claim 8, wherein the phantom tissue simulant surface consists of a silicone phantom tissue simulant surface.

12. The system of claim 8, wherein the at least one medical instrument is selected from a group consisting of: a needle assembly, a guidewire, a safety scalpel, a dilator and/or a catheter, the needle assembly and scalpel being blunted.

13. The system of claim 12, further comprising a spherical magnet connected to the catheter to allow for magnetic detection using the at least one sensor.

14. The system of claim 8, wherein the at least one sensor is configured to detect insertion and removal the medical instruments into and from the insertion channel.

15. The system of claim 8, wherein the at least one sensor includes an entry sensor and one or more additional sensors disposed along the insertion channel.

16. The system of claim 8, wherein the at least one sensor includes hall effect sensors.

17. A method of providing training in a medical procedure for central venous catheter insertion, comprising:
  providing a medical training system having:
    a user interface,
    a work surface;
    a camera configured to view the work surface;
    a phantom tissue simulant surface disposed in or on the work surface and in view of the camera when the camera,
    a plurality of medical instruments, at least one of the medical instruments being a needle assembly having a tip configured to pierce the phantom tissue simulant surface,
    an insertion channel disposed beneath the phantom tissue stimulant surface, the insertion channel having an opening of the insertion channel, the insertion channel extending from the opening to a distal end,
    at least one sensor operable to determine an insertion position of the tip of the at least one medical instrument and to sense an external downward force of the at least one medical instrument on the phantom tissue simulant surface, and
    at least one microprocessor in connection with the at least one sensor, the microprocessor configured to read and process information from the at least one sensor;
  locating an insertion hole beneath a phantom tissue simulant surface, the insertion hole configured to simulate a target vessel;
  performing a medical instrument manipulation by inserting the tip of the needle assembly through the phantom tissue simulant surface and into the insertion hole, the needle assembly comprising a syringe, an occlude hub, and a needle;
  sensing that the tip of the needle assembly has penetrated the phantom tissue simulant and the insertion hole and calculating a depth position of the needle assembly within the insertion hole using the at least one sensor;
  manipulating the needle assembly by disconnecting the syringe and the occlude hub from the needle assembly;
  providing a guidewire to be inserted into the insertion hole and calculating a depth position of the guidewire within the insertion hole through the at least one sensor;
  removing the needle from the insertion hole while leaving the guidewire placed in the insertion hole;
  performing an incision by applying an external downward force to a scalpel into the phantom tissue surface and calculating a depth position of the scalpel within the insertion hole using the at least one sensor;
  removing the scalpel from the insertion hole and sensing the removal of the scalpel from the insertion hole using the at least one sensor;
  performing a dilation by placing a dilator through the incision and into the insertion hole and calculating a depth position of the dilator within the insertion hole using the at least one sensor;
  removing the dilator from the insertion hole and sensing the removal of the dilator from the insertion hole using the at least one sensor;
  providing a catheter to be inserted into the insertion hole and calculating a depth position of the catheter within the insertion hole using the at least one sensor;
  removing the guidewire from the insertion hole and sensing the removal of the guidewire using the at least one sensor;
  securing the catheter in a fixed position within the insertion hole and calculating a depth position of the catheter within the insertion hole using the at least one sensor; and
  providing performance feedback and assessment using the user interface based on the calculations of the at least one sensor.

18. The method of claim 17, wherein through the use of a limit switch and two spring loaded push buttons, the device is capable of detecting the insertion and removal the medical instruments.

* * * * *